United States Patent [19]
Johnson

[11] Patent Number: 5,568,255
[45] Date of Patent: Oct. 22, 1996

[54] APPARATUS FOR CONTROLLING THE SCAN WIDTH OF A SCANNING LASER BEAM

[75] Inventor: Gary W. Johnson, Livermore, Calif.

[73] Assignee: The United States of America as represented by the United States Department of Energy, Washington, D.C.

[21] Appl. No.: 321,695

[22] Filed: Oct. 12, 1994

[51] Int. Cl.$^6$ .................................................. G01B 9/02
[52] U.S. Cl. ............................ 356/352; 356/345; 372/29
[58] Field of Search .................................. 356/345, 352; 372/29, 30, 31, 32

[56] References Cited

U.S. PATENT DOCUMENTS

| | | | |
|---|---|---|---|
| 4,947,398 | 8/1990 | Yasuda et al. | 372/29 |
| 5,353,115 | 10/1994 | McIntyre | 356/352 |

OTHER PUBLICATIONS

Schuda et al, "Direct Optical Measurement of Sodium Hyperfine Structure using a CW dye Laser and An Atomic Beam", Apr. 1973, applied physics, p. 360.

Primary Examiner—Frank Gonzalez
Assistant Examiner—Robert Kim
Attorney, Agent, or Firm—Miquel A. Valdes; William C. Daubenspeck; William R. Moser

[57] ABSTRACT

Swept-wavelength lasers are often used in absorption spectroscopy applications. In experiments where high accuracy is required, it is desirable to continuously monitor and control the range of wavelengths scanned (the scan width). A system has been demonstrated whereby the scan width of a swept ring-dye laser, or semiconductor diode laser, can be measured and controlled in real-time with a resolution better than 0.1%. Scan linearity, or conformity to a nonlinear scan waveform, can be measured and controlled. The system of the invention consists of a Fabry-Perot interferometer, three CAMAC interface modules, and a microcomputer running a simple analysis and proportional-integral control algorithm. With additional modules, multiple lasers can be simultaneously controlled. The invention also includes an embodiment implemented on an ordinary PC with a multifunction plug-in board.

3 Claims, 8 Drawing Sheets

APPARATUS FOR CONTROLLING THE SCAN WIDTH OF A SCANNING LASER BEAM

GOVERNMENT RIGHTS

The United States Government has rights in this invention pursuant to Contract No. W-7405-ENG-48 between the U.S. Department of Energy and the University of California.

FIELD OF THE INVENTION

The present invention relates generally to laser scan width, and more particularly to a laser scan width system that automatically controls the scan width of the laser to a resolution on the order of 0.1% or better.

BACKGROUND OF THE INVENTION

Many plasma diagnostic techniques use a swept-wavelength laser to obtain atomic absorption spectra from a plasma stream. Most of these measurements are dependent upon the scan width of the laser, typically measured in GHz. Since there are no instruments that measure scan width directly, the laser operator must attempt to manually adjust the scan width to specifications (within a few percent), and keep it there at all times. Results of many spectroscopic measurements, such as plasma density, are directly proportional to scan width. Two instruments are presently available to assist the operator in this scan width adjustment effort: wavemeters and Fabry-Perot confocal interferometers (F-Ps).

Wavemeters directly measure absolute wavelength by comparison with a reference light source or with a precision grating. However, only the most expensive and exotic wavemeters have sufficient resolution to measure the difference between the endpoints of a narrow scan, and even the best cannot track the wavelength as it rapidly changes.

Another way to directly measure scan width employs Fabry-Perot confocal interferometers (F-Ps). The F-P samples the laser beam at some point in the optical system. As the laser is scanned, the F-P interferometer produces a voltage pulse each time the wavelength crosses through a free-spectral resonant mode of the interferometer's cavity. The laser operator can observe the F-P pulses on an oscilloscope and attempt to visually count them, then adjust the laser until the proper number appears. A simple digital counter, synchronized with the scan, could also help to automate the counting process. With a Coherent, Inc., model 216 Fabry-Perot interferometer, a pulse occurs every 300 MHz. For example, with a scan of 3 GHz, 10 F-P intervals appear during each scan. The laser operator could then trim the scan width by manually adjusting the scan width knob on the laser's control chassis. However, the precision of this measurement is only ±10% (one in 10). Thus, a 10% peak error in any wavelength-dependent measurements may be expected. Also, the operator must periodically adjust the laser to compensate for drift. For this reason, an improved, automated measurement and control system for scan width using a real-time control computer and some specialized CAMAC (Computer Automated Measurement and Control, IEEE 595) modules designed specifically for this application would be desirable. The present invention presents such a system.

SUMMARY OF THE INVENTION

In accordance with the present invention there is shown a system and method for automatic laser scan width control of a tunable laser where there is a user selected set-point of the desired scan width. In that type of laser a primary light beam from a laser source is directed to a Brewster plate that is driven by a galvanometer with the laser scan width of a secondary light beam exiting the Brewster plate being determined by the angle through which the galvanometer is displaced. As the primary light beam passes through the Brewster plate the scan width of the primary light beam changes as a result of the instantaneous path length through the Brewster plate. That path length is determined by the angle of the Brewster plate to the primary light beam forming the secondary light beam that exits the Brewster plate with the secondary light beam having a scan width that is determined by the scan width of the primary light beam as modified by the Brewster plate. In order to perform that control, an interferometer, aligned to continuously receive the secondary light beam, produces an electronic pulse each time a wavelength of the secondary light beam crosses through a free-spectral resonant mode of the resonant cavity of the interferometer. Those electronic pulses from the interferometer are coupled to a controller where the laser scan width of the secondary light beam is calculated, and then, from the calculated laser scan width, the amplitude of a next scan signal to be applied to the galvanometer is calculated.

DESCRIPTION OF THE EMBODIMENTS OF THE PRESENT INVENTION

First Embodiment

Figure 1:
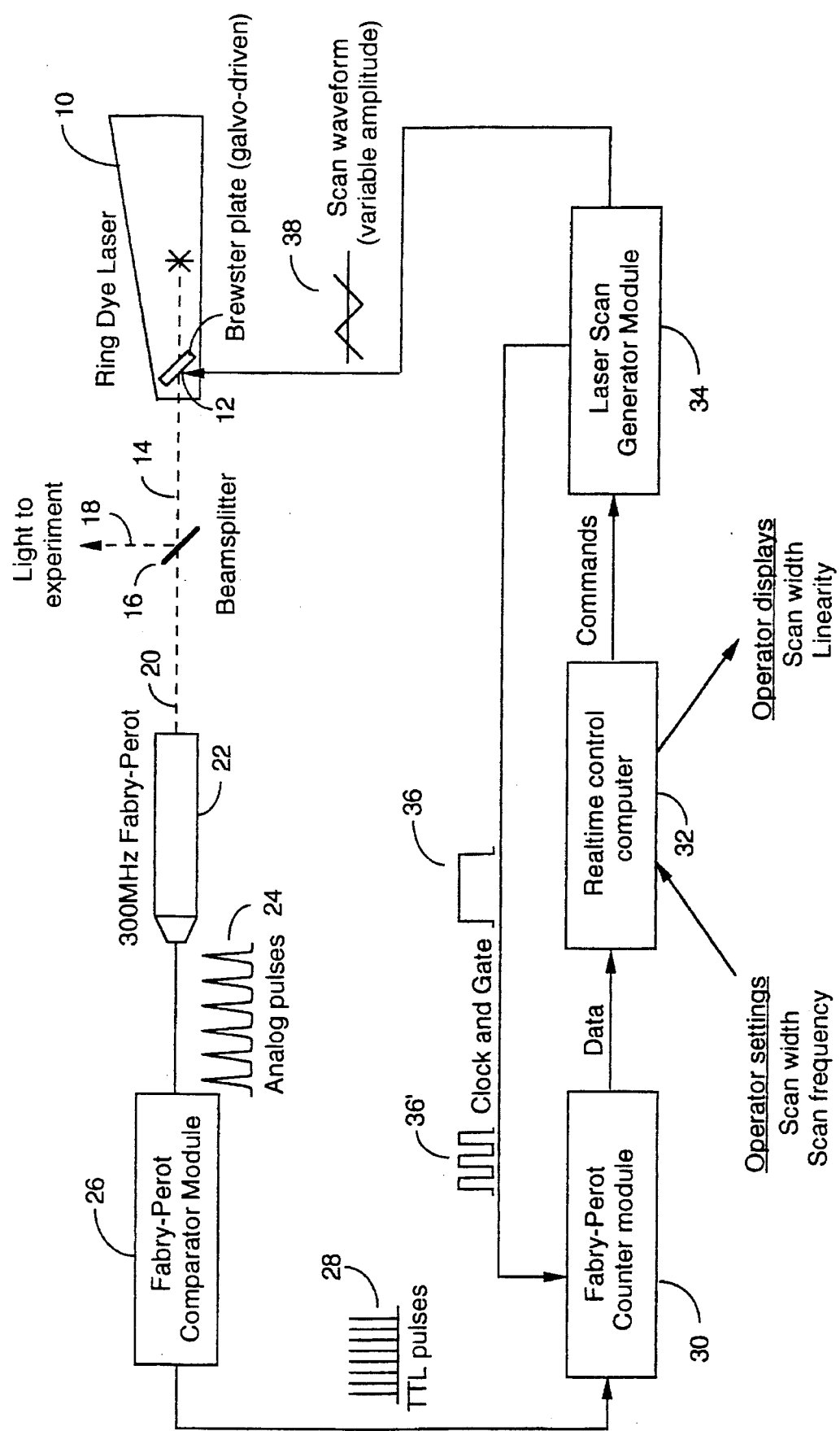
FIG. 1 is a schematic block diagram representation of a first embodiment of the present invention.

The main components of the scan width control loop system of the first embodiment of the present invention are diagrammed in FIG. 1. Laser 10 provides the source of coherent light with the light exiting laser 10 by means of galvanometer-driven Brewster plate 12 as beam 14. Beam 14 is directed to beamsplitter 16 where a portion of the light is reflected to an experiment as beam 18, and the remainder of the light of beam 14 passes through beamsplitter 16 as beam 20. Beam 20 in turn is applied to F-P interferometer 22 to produce F-P pulses 24 each time the wavelength of beam 16 crosses through a free-spectral resonant mode of the cavity of F-P interferometer 22. In turn, the analog pulses 24 from F-P interferometer 22 are conditioned by the Fabry-Perot comparator module 26 to provide signal 28 that has logic compatible levels for the remainder of the system (in the experimental implementation of this embodiment the logic used was TTL). The pulses of signal 28 are fed to the Fabry-Perot counter module 30, which performs the actual measurements. Jumping ahead briefly, laser scan generator module 34 generates the laser scan ramp signal 38 (with programmable amplitude and frequency), and timing pulses 36 and 36' for other data acquisition equipment used in the system, such as F-P counter module 30. Real-time computer 32 is programmed (Appendix I and FIG. 5 as discussed below), using the data from F-P counter module 30, to calculate the scan width and scan linearity, and the error in scan width relative to the desired set-point value of beam 14 from laser 10 where the set-point is the scan width desired by the user. Computer 32 is programmed to use those values to determine the error in the measured scan width (measurement vs. set-point) and then, based on the error calculations, sends a command to laser scan generator module 34. In response to that command, scan generator module 34 adjusts the ramp amplitude of scan waveform 38 proportionally until laser 10 scans the desired range of wavelengths. To complete the loop of the system of the present invention, modified scan waveform 38 is applied to the galvanometer-driven Brewster plate 12 of laser 10. Thus, the operator can see, in real-time, the scan width and linearity of laser 10 with high accuracy. Also, if laser 10 should suddenly mode-hop off of the desired center wavelength, the measured linearity will instantaneously be very poor. Such a condition is easily detected by computer 32 (see Appendix I and discussion of FIG. 5 below), which then generates an alarm to warn the operator that laser 10 needs attention.

Absolute accuracy is limited by the calibration of Fabry-Perot interferometer 22, which is performed in an optical calibration facility that has traceability to international standards. Measurement resolution of this system is limited by the number of timing pulses generated by laser scan generator module 34 as discussed below. In one operational embodiment, say 1024 pulses are generated during each scan, which implies a resolution better than 0.1% (one part in 1024=0.09766%). In that embodiment, the actual scan width data collected, while laser 10 was under control, indicated a peak deviation from the set-point of ±0.6%, and long-term stability was within 0.1%.

Scanning the Laser

Coherent model CR-699 ring-dye lasers (10) have often been used experimentally for diagnostics systems. These lasers feature active stabilization and quick tunability over tens of GHz, which is vital to applications in plasma physics. Each laser 10 is manually aligned and adjusted until it begins to operate, then it is tuned to the desired center wavelength by an automatic tuning computer which is available as an option for the CR-699 series. The tuning computer of laser 10 adjusts several optical elements until the performance of the laser is optimized, then puts laser 10 on line. One of the optical elements in laser 10 is a Brewster plate 12, which is a small glass plate near the output of the ring, that is driven through a small angular range by a galvanometer (not shown), which in turn receives drive current, in the form of waveform 38 from laser scan generator module 34. Rotation of Brewster plate 12 changes the optical path length through plate 12, which changes the cavity length in laser 10 with the optical wavelength produced by laser 10 being proportional to the cavity length. Thus, as ramp voltage 38 rises and falls linearly with respect to time, laser 10 is scanned over a proportional range of wavelengths in a linear fashion.

Figure 2:
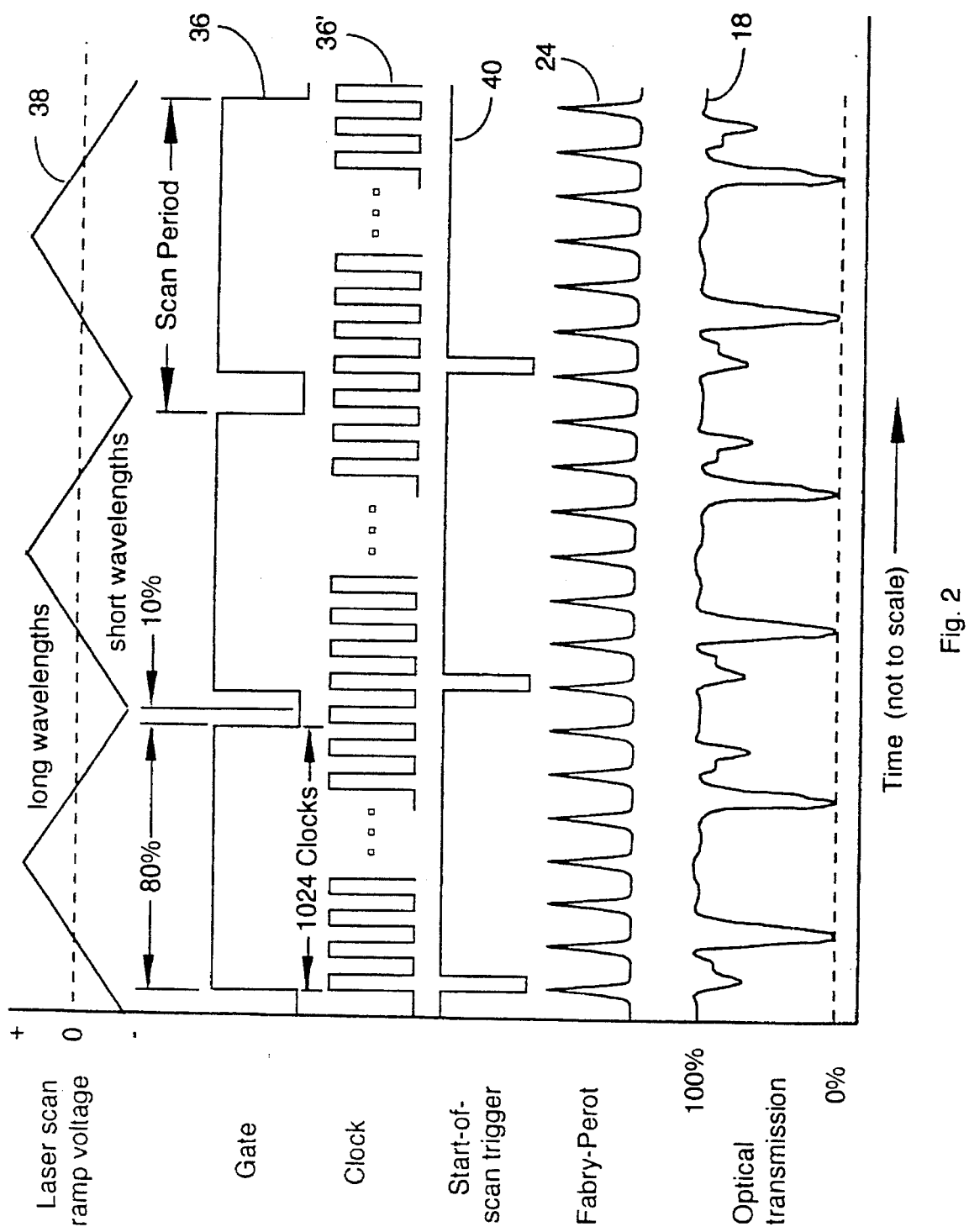
FIG. 2 is a timing diagram of the family of signals relative to each other of the embodiment of FIG. 1.

Timing signals 36 and 36', for the system, are generated by laser scan generator module 34, as shown in FIG. 2. During a typical scan, the ramp voltage 38 (a triangular wave) increases and decreases linearly with time, the amplitude and duration of which is programmed through CAMAC commands from control computer 32. The middle 80% of scan ramp 38 is bracketed by the gate signal 36, during which laser 10 is expected to produce a linear change of wavelength with scan voltage. When a gate 36 interval begins, a negative-logic trigger pulse 40 is produced, which initiates data collection in any external diagnostics, such as spectrometers. Clock 36' is active at all times, and is used to synchronize F-P counter module 30 with exactly 1024 clock 36' pulses (as per the above example) produced during each gate 36 high intervals. All of the signals shown in FIG. 2 are distributed throughout the diagnostics laboratory area for system synchronization.

During the middle 80% of scan waveform 38 (gate 36 high interval), modified F-P pulses 24 (i.e. pulses 28) are accumulated in the F-P counter module 30, along with clock 36' pulses which are used to make a high resolution measurement of each F-P pulse 24 spacing and position within the scan. On command from control computer 32 via laser scan generator module 34, F-P counter module 30 is armed, after which a data acquisition cycle is triggered by gate signal 36. When a single gate 36 interval is complete, computer 32 then collects the data and calculates scan width and linearity. The amplitude of ramp waveform 38 is then adjusted by computer 32 (through laser scan generator module 34) to correct any error in scan width of beam 14 (i.e. the amplitude of scan waveform 38 is adjusted as required to make the number of F-P pulses 24 in each scan match the desired number that corresponds to the selected scan width set-point).

Detailed Hardware Description

The Fabry-Perot interferometer 22, and associated equipment are available from several manufacturers with Coherent model 216 used in the experimentation and testing of the present invention. The Coherent CR-699-series laser 10 could also be replaced with another brand, or any source of coherent light that can be scanned by an analog voltage (i.e., a laser diode system). Control of the various modules has been implemented on a DEC LSI-11 microprocessor under the RSX-11M+ operating system. Original development and testing was done on a Macintosh SE computer 32 running LabVIEW® software from National Instruments, with a National Instruments GPIB (IEEE-488) interface to a CAMAC crate. The measurement and control program could also be implemented on any general-purpose microcomputer system capable of interfacing to a CAMAC crate.

Another way to build the system is discussed below as the second embodiment. The second embodiment incorporates a commercial, multifunction, input/output interface board with analog and digital signal connections, installed in a personal computer. These low-cost boards, such as the National Instruments MIO-16 series, can be programmed directly in the LabVIEW® graphical programming language which would also serve as the user interface. Thus, a complete implementation of the scan width controller of the second embodiment could consist of a PC, a plug-in input/output interface board, a Fabry-Perot interferometer, and the program described above.

Laser Scan Generator Module 34

Figure 6:
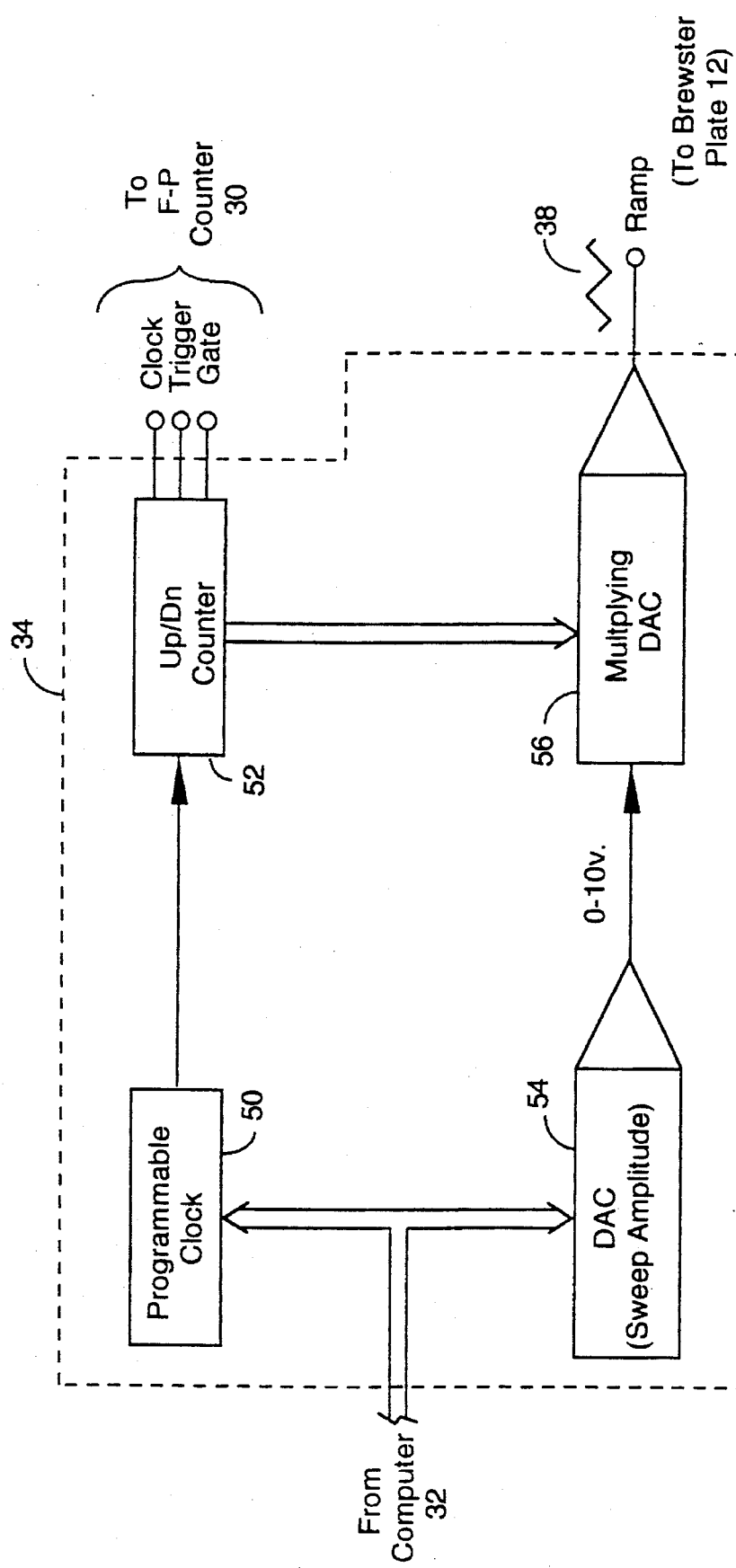
FIG. 6 is a simplified block diagram of the laser scan generator module of the first embodiment of the present invention.

The laser scan generator module 34 is a single-width CAMAC module designed specifically for the particular laser diagnostic system, and a simplified block diagram thereof is provided in FIG. 6. As shown in FIG. 6, module 34 includes a programmable clock 50 and a D-A converter 54, each under the control of computer 32. Programmable clock 50 typically includes a quartz oscillator followed by a programmable divider (not shown) with computer 32 controlling the integer by which the clock signal from the oscillator is divided to make the necessary adjustments to the various system signals. Similarly, D-A converter 54 provides the sweep amplitude for the scan waveform ramp 38. The clock signal from programmable clock 50 is in turn applied to an up/down counter 52 to generate the clock, trigger and gate signals that are applied to F-P counter module 30. The final block of the laser scan generator is a multiplying D-A converter 56 which receives the sweep amplitude from D-A converter 54 and the clock signal from up/down counter 52 to generate the scan waveform ramp 38 to drive Brewster plate 12.

The function of module 34 is to produce all of the timing signals, the ramp waveform 38, and synchronize simulation data for testing of a plasma diagnostics system with each function (scan period and ramp amplitude) programmable via CAMAC commands from computer 32. In the experimental system, the scan period was normally 0.1 sec., but was sometimes 1.0 sec., and the triangular wave scan waveform 38 amplitude was normally about 5.0 v peak-peak.

Each time the scan of laser 10 switches directions, the dye laser's Brewster plate 12 tends to overshoot its ideal position, resulting in some aberrations in the otherwise smooth, linear scan. To eliminate this artifact, scan generator 34 produces gate pulse 36 that is high (active) during the middle 80% of the scan interval thus effectively zeroing out those artifacts, and during the active scan interval of gate pulse 36, scan generator 34 produces a selected number (1024 is a convenient number that was used experimentally) clock pulses 36'. It is during that active interval that all data is collected with the other 20% of the scan being ignored.

Fabry-Perot Comparator Module 26

Figure 7:
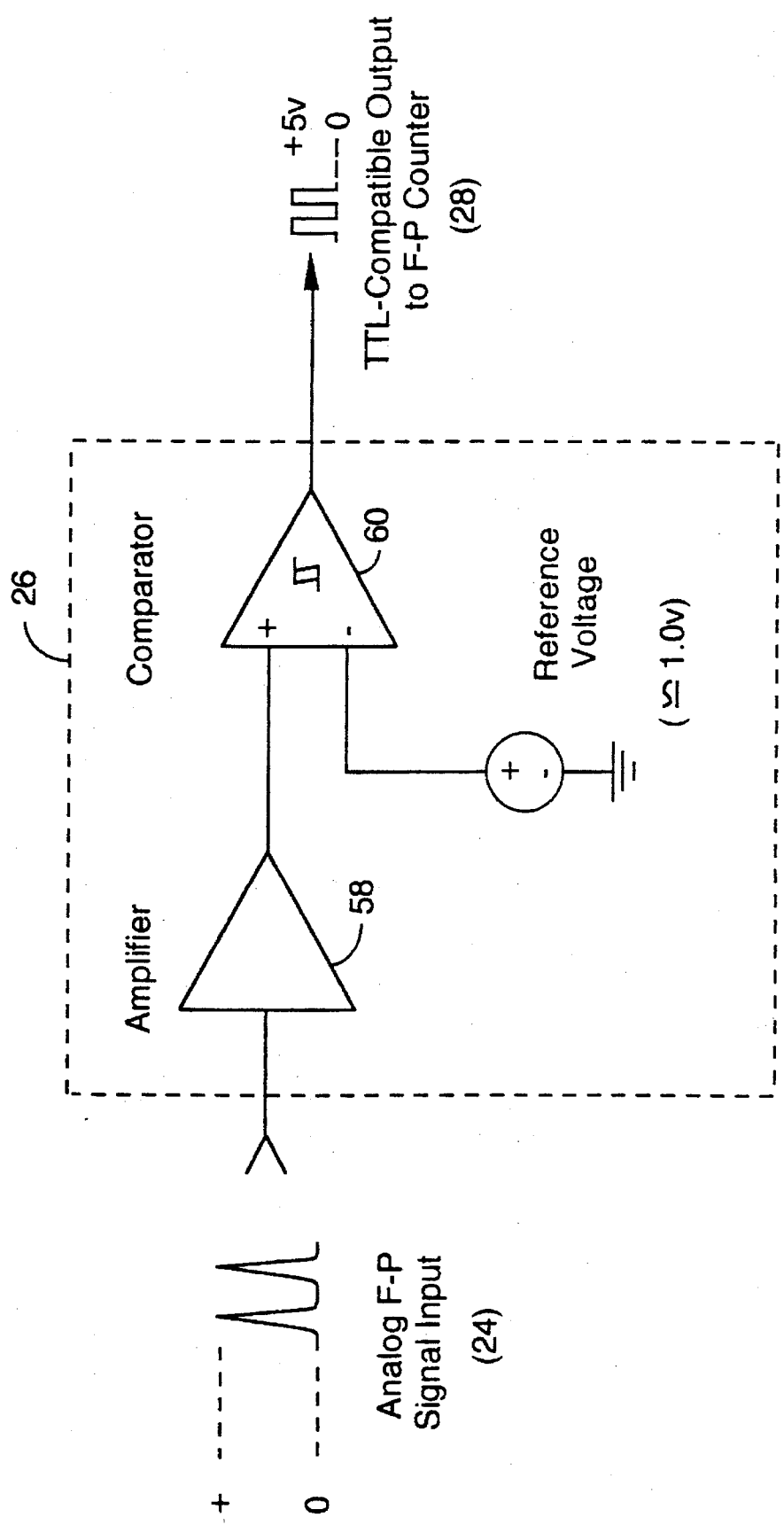
FIG. 7 is a simplified circuit diagram of the F-P comparator module of the first embodiment of the present invention.

Fabry-Perot comparator module 26 is a double-width CAMAC module designed specifically for laser diagnostics systems with a simplified circuit diagram thereof shown in FIG. 7. In FIG. 7, the F-P comparator module 26 is shown containing an amplifier 58 which receives the analog output pulses 24 from F-P interferometer 22 and amplifies that signal as necessary. The amplified analog signal from amplifier 58 is then applied to comparator 60 which squares-up the amplified analog F-P signal to convert it to a logic pulse train 28 of the appropriate amplitude (TTL 5 volts peak was selected for the experimental system).

Thus, the function of comparator module 26 is the conditioning of the raw analog F-P signal 24, from F-P interferometer 22, using a comparator with hysteresis to convert F-P signal 24 into a digital signal 28 for application to F-P counter module 30. Comparator 60, in order to perform its function, includes adjustable thresholds and fixed hysteresis. In the experimental implementation the output signals were selected to be 5 v TTL compatible.

Fabry-Perot Counter Module 30

The Fabry-Perot counter module 30 counts and stores the number of equally tempered clock pulses 36' between the incoming F-P pulses 28 during an interval defined by gate signal 36. This function is performed to determine scan widths of laser 10 in real time. Then, at the end of a scan (i.e. when gate signal 36 changes state) the accumulated totals of the number of clock pulses between adjacent F-P pulses 28 are read-out by computer 32.

Figure 8:
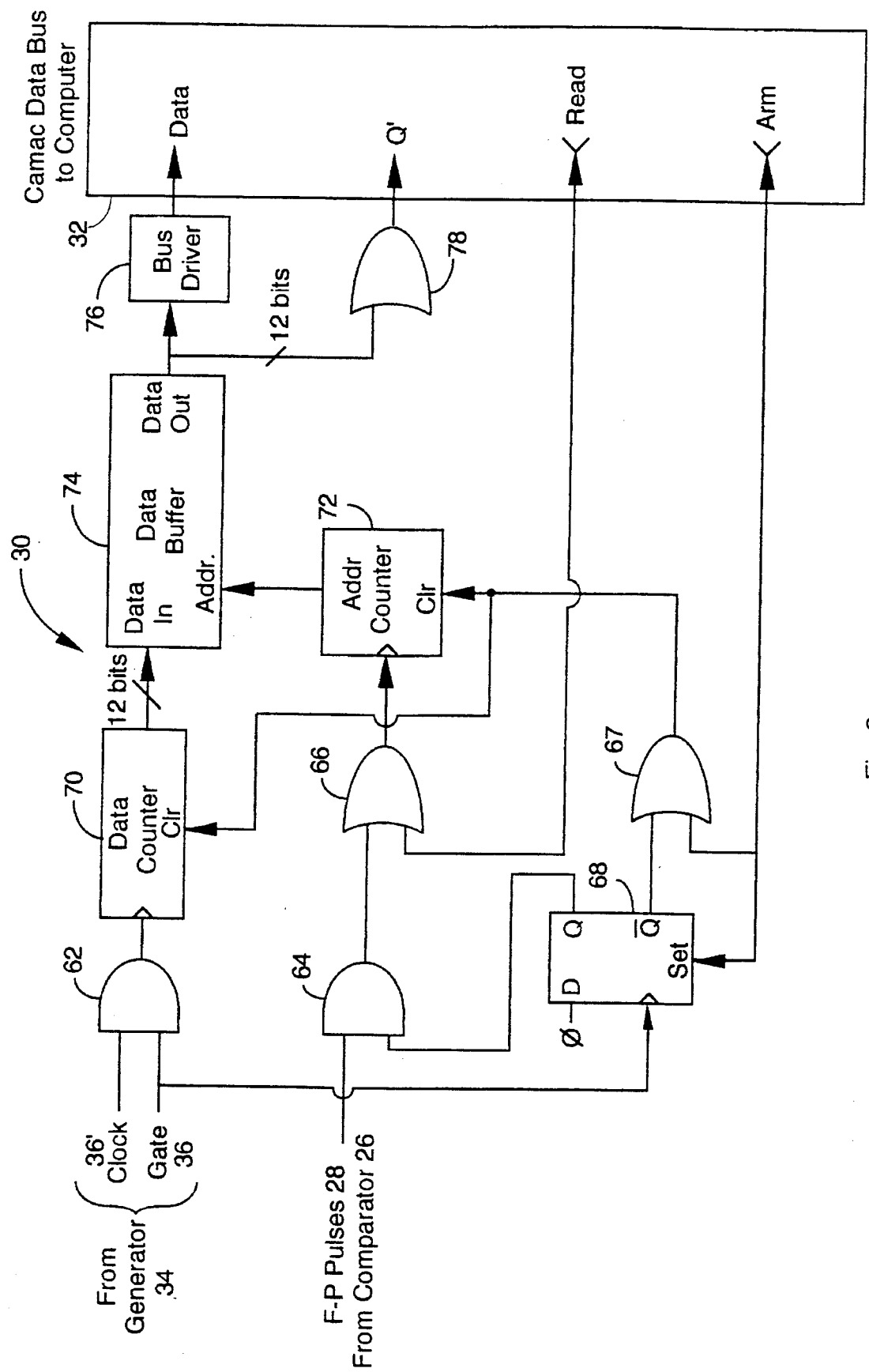
FIG. 8 is a simplified block diagram of a single channel F-P counter module of the first embodiment of the present invention.

A simplified block diagram of a single channel F-P counter module 30 is shown in FIG. 8. In that block diagram, the clock 36' and gate 36 signals from laser scan generator module 34 are applied to clock AND gate 62, and the F-P TTL pulses 28 from F-P comparator module 26 are applied to trigger AND gate 64.

To begin a data collection cycle, an "ARM" signal from computer 32 sets the Q output of flip-flop 68 to a high state, which enables AND gate 64. The inverse of the "ARM" signal (Q-complement), via OR gate 67, is applied to the "clear" inputs of data counter 70 and address counter 72, which resets them to an empty state. During a sweep cycle from open to close (i.e., when gate signal 36 is high), data counter 70 keeps a cumulative count of the clock pulses from clock AND gate 62, and address counter 72 is incremented whenever an F-P pulse 28 is received via F-P pulse AND 64 and OR gate 66. When address counter 72 is incremented, the current clock pulse count from data counter 70 is stored in data buffer 74 at a new address obtained from address counter 72. Twelve bits of data (for the experimental embodiment) are stored in the data buffer 74 for each F-P pulse 28. When gate signal 36 goes low, the Q output of flip-flop 68 goes low disabling AND gate 64, thereby preventing further incrementing of address counter 72. The Q-complement output of flip-flop 68 simultaneously goes high, passes through OR gate 67 to the "clear" inputs of data counter 70 and address counter 72, which resets them to an empty state in preparation for a data readout. This ends the data collection cycle, which may not begin again until the "ARM" signal is again received.

Data from data buffer 74 is read out to computer 32 via bus driver 76. In response, computer 32 sends a "READ" pulse via OR gate 66 to address counter 72 to increment the count of address counter 72 and thus the address of data buffer 74. This makes the data at the next address location available at the output of data buffer 74. OR gate 78 also monitors the data from each address location of data buffer 74. If the data value at the data location is non-zero, OR gate 78 causes the logic level of the Q' signal to stay high. At the first address of data buffer 74 at which the data value is zero, OR gate 78 switches the Q' signal low, acting as an end-of-data indicator for computer 32.

Data stored in data buffer 74 can be represented by a simple list containing the clock pulse number present when each conditioned F-P pulse 28 arrives at gate 64. For instance, if there were five evenly-spaced conditioned F-P pulses 28 during the logical high time of gate 36, the numbers in data buffer 74 might be:

$$(100, 300, 500, 700, 900) \qquad (1).$$

This list assumes that the first conditioned F-P pulse 28 arrived 100 clock periods into the period of the logical high time of the gate pulse 36, the second F-P pulse at 300 clock periods, the third at 500 clock periods, the fourth at 700 clock periods and the fifth at 900 clock periods.

Real-Time Control Computer 32

Computer 32 can be implemented with any personal computer and programming language to execute a standard feedback control algorithm (proportional-integral), allowing the wavelength set-point to be changed at any time.

Computer 32 Calculations

To calculate the scan width from the clock count data, the following formula is used:

$$\text{ScanWidth} = ((N-1)/(\text{Data}[N] - \text{Data}[1])) \times FSR \times N\text{Clocks} \qquad (2)$$

Where:
- ScanWidth is the calculated scan width in GHz;
- N is the number of F-P events in the register (5, in this example);
- Data[i] is a value in the register (e.g., Data[2]=300);
- FSR is the free spectral range of the Fabry-Perot 22 (0.3 GHz, in the experimental case); and
- NClocks is the number of clock pulses that occur during the gate pulse 36 high interval (number of clock pulses during scan).

So, for the example here with each scan containing 1024 clock pulses, the scan width is:

$$\text{ScanWidth}=((5-1)/(900-100))\times 0.3 \times 1024 = 1.54 \text{ GHz} \quad (3)$$

Linearity can be assessed by observing the distribution of count differences among pairs of F-P events. For instance, in the example above, all four differences between sequential counts in (1) were exactly 200 counts, thus the scan was perfectly linear. Various statistical techniques could be applied, such as linear regression, wherein the standard deviation might be an appropriate measure of linearity.

The calculations discussed above, however, only measure the scan width and linearity. To control scan width, computer 32 must compare the measured scan width with the operator-entered set-point, or desired scan width value. If a difference (error) exists, an appropriately-adjusted value for the amplitude of scan waveform 38 is sent to laser scan generator module 34. This constitutes ordinary negative-feedback, closed-loop control, implemented with any well-known discrete-time control algorithm. In the experimental system of the first embodiment of the present invention a proportional-integral discrete time control algorithm was used to minimized both short-and long-term errors in scan width.

Computer 32 Calculation Details

Figure 5:
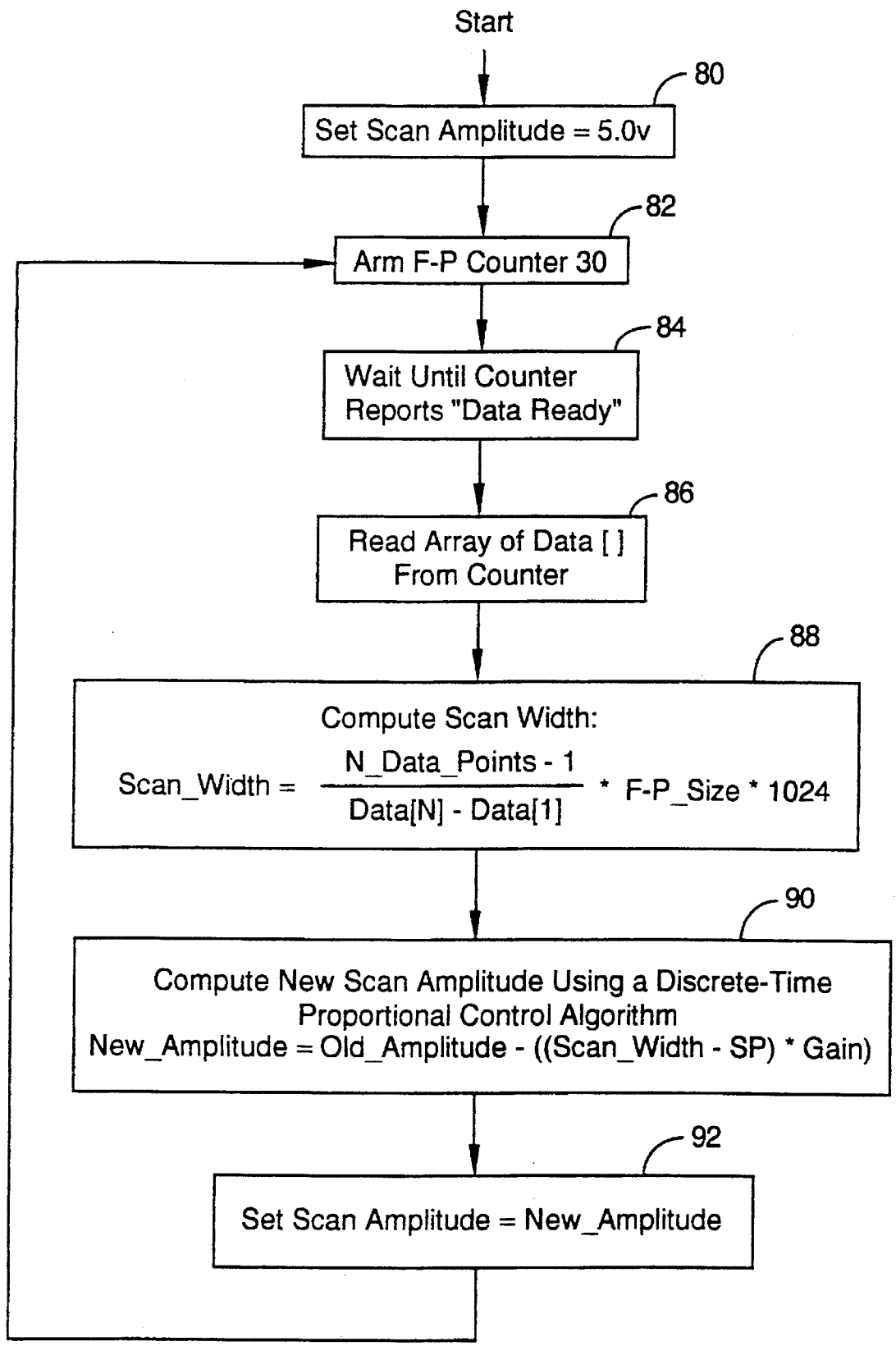
FIG. 5 is a simplified flow chart of the calculations performed by the real time computer in FIG. 1.

FIG. 5 is a block diagram of the calculation flow that is performed by computer 32. Beginning at block 80 a peak-to-peak amplitude of scan waveform 38 is entered, or read from memory as an initial value for the system of this embodiment with the maximum amplitude of scan waveform 38 limited by the maximum input peak-to-peak voltage range of the galvanometer that drives Brewster plate 12 in laser 10. In the experimental system of this embodiment of the present invention, that maximum value was 5.0 v.

The next step (block 82) is to arm F-P counter module 30 via laser scan generator module 34 with a high gate signal 36. As discussed above, with gate signal 36 high, counter 30 collects data relative to the number of F-P pulses between each clock 36' pulse. While the data acquisition is occurring in counter 30, computer 32 is in a wait mode (block 84) until the "end of data indicator" (Q' switching to the low state) is received from counter 30.

Following receipt of the "end of data indicator", the data acquired by counter 30 during the previous data collection period is transferred from counter 30 to computer 32 (block 86). Using that data, computer 32 calculates the scan width (block 88) using equation (2) above. Next a new scan amplitude is calculated (block 90) using the calculated scan width from block 88 with a discrete-time proportional control algorithm such as the following.

$$\text{New Amp} = \text{Old Amp} - ((\text{Scan Width} - \text{SetPoint})*\text{Gain}) \quad (4)$$

In equation (4), SetPoint is the desired scan width selected by the user, and Gain is the controller gain that is experimentally selected to provide a stable scan width. Experimentally, the value of Gain was determined to range between 5 and 200, with 50 being a typical value. The amplitude of scan waveform 38 is then reset (block 92) to the lesser of the newly calculated New Amp or the maximum value permitted by the galvanometer drive of Brewster plate 12. At that point control returns to block 82 to again arm counter 30 for the next data collection cycle.

Experimental Performance

Normal operating conditions in the laser laboratory were: wavelength approximately 500 nm, scan rate 10 Hz, and scan width 6 GHz. The Coherent CR-699 laser 10 exhibited excessive non-linearity and a tendency to mode hop at faster scan rates. (Laser diodes have no such limitation; the control system of the first embodiment of the present invention worked reliably for scan rates in the KHz range). Also, laser 10 needed careful manual and computer-aided adjustment to ensure usable stability before automatic scan width control could be realized with this adjustment system having been used at other visible and ultraviolet (UV) wavelengths (UV setup required the use of frequency doubling optics in laser 10).

Figure 3:
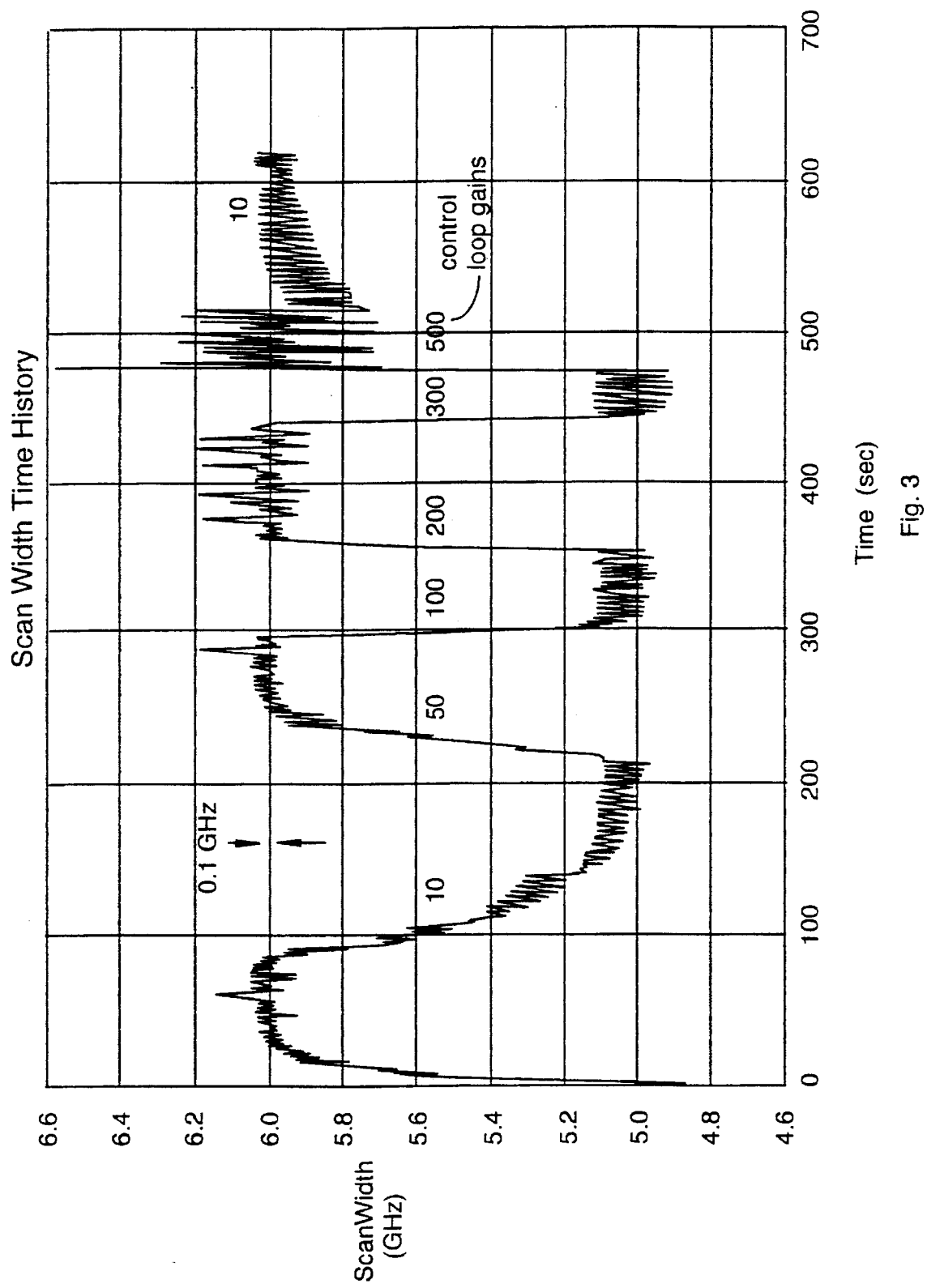
FIG. 3 is an experimental plot of the scan width time history of the embodiment of the present invention of FIG. 1 with various control loop gains.

FIG. 3 shows the experimental response of the control system of the first embodiment to changes in the set-point, which was alternated between 5.0 and 6.0 GHz. Proportional system gain was increased throughout the experimental run to observe the effects on control accuracy. A gain of about 50 was ultimately selected, experimentally, as a compromise between settling time, stability, and noise rejection. Longer-term testing demonstrated essentially zero measurable drift (<0.1%) over a period of 30 minutes. The practical limitation in such testing was that the ring dye laser 10 tended to drift out of alignment to the point that it had to be taken off-line for retuning about every hour or so.

Second Embodiment Using Analog Signal Acquisition

To this point the description has covered a system of the first embodiment of the present invention that uses digital hardware counting techniques. This second embodiment utilizes an analog technique for use when the present invention control system is built around a PC with a plug-in multifunction board as illustrated in the schematic block diagram of FIG. 4. In the top half of FIG. 4, laser 10 through the analog F-P pulses 24 from F-P interferometer 22 are again shown and they operate in the same way as in the digital first embodiment of FIG. 1. The main difference between this embodiment and the first embodiment of FIG. 1 is that there are no digital signals (clock and gate) generated or distributed externally from the PC and the boards plugged thereinto. Instead, this technique relies on high-speed analog-to-digital converter (ADC) 44 (on multifunction plug-in board 42—e.g. National Instruments MIO-16) to digitize the raw analog F-P waveform 24 and record the digitized signal for later use, without the need for external signal conditioning or F-P comparator module 26 as in FIG. 1. Simultaneously and synchronously with the processing of F-P waveform 24 by ADC 44, scan waveform 38 is generated by digital-to-analog converter (DAC) 46 (also on multifunction plug-in board 42), typically as a triangular wave. Internal synchronization between DAC 46 and ADC 44 (using a common clock signal) is a standard feature of plug-in board 42 used here. Thus, the clock internal to PC 48 (serves the same function as the 1024-pulse external clock in the digital first embodiment of FIG. 1) provides a high-resolution "ruler" for the measurement of each F-P pulse 24 interval.

F-P pulse 24 positions are determined by examination of the digitized F-P waveform 24 recorded by ADC 44 with an ordinary peak detection algorithm—one that uses threshold comparison. The peak detector function built into the LabVIEW® software on PC 48 worked well in simulations of the second embodiment of the present invention. The output of such an algorithm is a list of sample numbers representing the center of each peak with this list being identical to the one stored in the digital F-P counter module 30 of the first embodiment of FIG. 1, and the data analysis for scan width determination is therefore the same as in equation 2 above.

Scan width is then adjusted by changing the amplitude of scan waveform 38 with scan waveform 38 being generated by simple arithmetic (for a ramp) or by an arbitrary mathematical function or table (for nonlinear scan waveforms) via DAC 46 by the LabVIEW®, or other, software on PC 48. The computed scan waveform 38 is then loaded into an output buffer of DAC 46, which proceeds to generate an analog output scan waveform 38 that drives the galvanometer that causes Brewster plate 12 to scan.

Variations

In the first embodiment in FIG. 1, higher resolution is feasible by increasing clock rate 36' from laser scan generator module 34. As discussed above, in the first embodiment experimental system 1024 pulses are produced during a scan when gate signal 36 is high. By increasing the clock rate (say, by a factor of 100), the resolution is correspondingly increased. The transducer, Fabry-Perot interferometer 22, quickly becomes the limiting factor for both accuracy and resolution in such a system. Also note that Fabry-Perot interferometers are available for almost any wavelength of light from ultraviolet through infrared. At least two F-P pulses 24 must be acquired per scan, with the upper limit on the number of pulses per scan being determined by the number of clock pulses 36' per scan and the number of memory locations in data buffer 74 of F-P counter module 30 (256 in the implementation as discussed above).

A feature easily added to the first embodiment is linearity control with F-P counter module 30 maintaining a complete record as to when each F-P pulse 24 occurred during the scan utilizing clock pulses 36' from laser scan generator module 34. This data record thus constitutes an accurate, piecewise-linear representation of laser wavelength versus time. A simple polynomial least-squares curve fit, applied to that data, with the coefficients from that fit used to generate a complementary laser scan waveform 38, thus linearizes a non-ideal laser system.

Another feature that could be added to the program of computer 32 is the ability to handle non-linear scan waveforms. For instance, it may be desirable to scan laser 10 with a sinusoidal waveform to maximize the scan rate since the sharp transitions of triangular waves tend to perturb the internal control loops of a laser. Again, data from F-P counter module 30 is used as a detailed time history of the wavelength of beam 14 and is therefore independent of the shape of scan waveform 38. The control program on computer 32, therefore can fit a sinusoid, or other mathematical function, to the incoming data, as well as it can a straight line.

Figure 4:
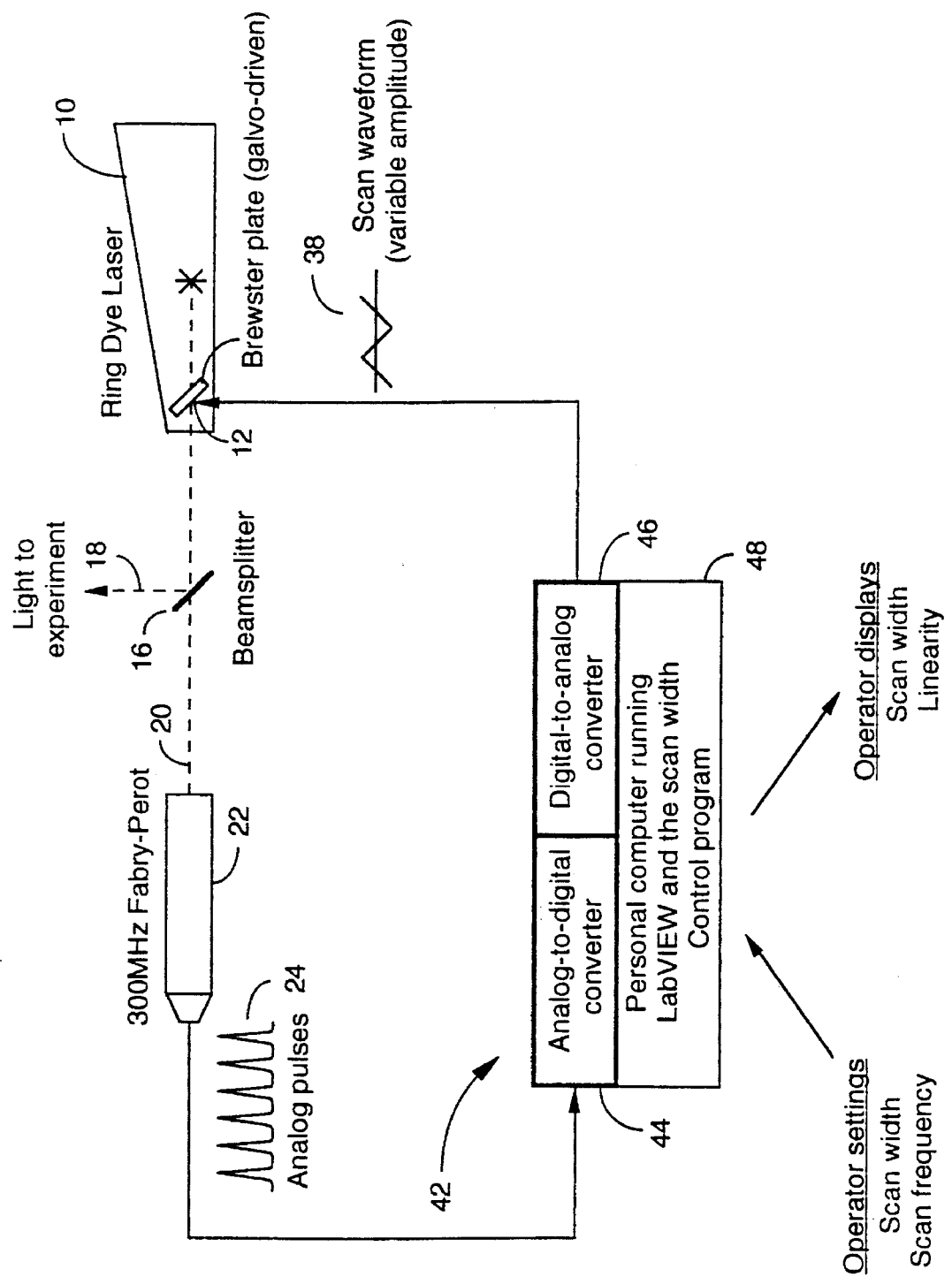
FIG. 4 is a schematic representation of a second embodiment of the present invention.

Hardware implementations for future systems may or may not use the CAMAC format with a general-purpose computer. The second embodiment personal computer-based analog solution, described with the aid of FIG. 4, is an effective way to implement one of those systems. A commercialized, packaged instrument with all necessary interfaces built-in and a preprogrammed microprocessor, would be more convenient in many laboratory situations. In such a system, operators would enter Fabry-Perot calibration information, the output voltage requirement, and a scan width set-point with data being collected, analyzed, and displayed, and made available on a computer-compatible interface port such as IEEE-488 (GPIB). This port could also be used to set-up and adjust the system. A dedicated computer would also permit high-performance control, with rapid response time, and extensive data reduction capabilities.

Further, the system of both embodiments of the present invention will work with any well-behaved scanned laser 10, such as dye and diode lasers (i.e., diode lasers do not exhibit mode-hopping or other abrupt stepwise wavelength changes while being scanned).

The foregoing description of the preferred embodiments of the present invention have been presented for purposes of illustration and description. It is not intended to be exhaustive or to limit the present invention to the precise form disclosed, and obviously many modifications and variations are possible in light of the above teaching. The embodiments were shown and described in order to best explain the principles of the present invention and its practical application to thereby enable others skilled in the art to best utilize the invention in various embodiments and with various modifications as are suited to the particular use contemplated. One such modification could be the inclusion of a multiplicity of channels with each using the same timing and pulse signals as in the first embodiment, or the inclusion of a multiplicity of multi-purpose boards in the PC of the second embodiment without modification of each channel individually as discussed above for the single channel implementations. Therefore, it is intended that the scope of the invention be defined only by the claims appended thereto.

---

APPENDIX I

```
PROGRAM Calculate_Scan_Width;
CONST    Max_Clocks =        1024;      (* number of clocks in the gate period *)
         FP_Size =           0.3;       (* 0.3 GHz per FP pulse cal factor *)
         Max_FP =            100;       (* No more than 100 FPs per scan *)
VAR Data:         Array[1 ... Max_FP] OF 1 ... Max_Clocks; (* Input *)
    FP:                      1 ... Max_FP;    (* Number of data points *)
    Scan_Width:   real;                       (* The result *)
    Peak_Error:   integer; (* Peak nonlinearity error in scan *)
PROCEDURE Get_Data_From_CAMAC (
         VAR    Data:        Array[1 ... Max_FP] OF 1 ... Max Clocks; ):
(* Arm the FP counter module, wait for data ready, then fill Data array
with count data *)
CONST    Time_Limit = nnn; (* Maximum time to wait for data *)
         Number_Of_Channels = 3; (* 3-laser module *)
VAR i:            integer;
    Init_Time:    integer;
    Ready:        0 ... 1;
BEGIN
    (* Initialize data array. Must be set to all zeros for main program
to detect end of data. *)
    FOR i := 1 to Max_FP DO Data[i] := 0;
    Arm_FP_Counter( F0A1 );
    Init_Time := Time; (* Store initial time *)
```

APPENDIX I

```
    (* Wait for data ready *)
    ready := Read_Ready_From_FP_Counter( F1A1 );
    WHILE (Time - Init_Time < Time_Limit) AND (ready = 0)
    DO ready := Read_Ready_From_FP_Counter( F1A1) ;
    IF (Time - Init_Time < Time_Limit)
    THEN (* Data can be read *)
    FOR i := 1 to Number_Of_Channels DO
            Read_Data_From_FP_Counter_Q-stop( F2Ai, Data );
    ELSE (* Timeout occured - leave data array null & bail out *);
END; (* Get_Data_From_CAMAC *)
PROCEDURE Scan_Linearity(
            Data:       Array[1 ... Max_FP] OF 1 ... Max_Clocks; (* Input *)
            FP:         1 ... Max_FP;    (* Number of data points *)
      VAR Peak_Error:   Integer; (* Result to return *) );
(* Calculate peak error in scan, assuming that scan is nearly linear to
begin with. Error is measured in "clocks". A perfect scan will show an
error of 1, due to quantizing.
*)
VAR     Avg:    Integer;        (* Nominal # of clocks between FP pulses *)
        Delt:   Integer;        (* # of clocks between an FP pulse pair *)
        Error:  integer;        (* Error relative to Avg *)
        i:      integer;
BEGIN
    Avg := (Data[FP] - Data[1]) / (FP - 1);
    Peak_Error := 0;
    FOR i := 2 TO FP DO (* Search for biggest difference from Avg *)
    BEGIN
        Delt := Data[i] - Data[i-1];
        Error := abs( Delt - Avg );
        IF Error > Peak_Error THEN Peak_Error := Error;
    END
END; (* Scan_Linearity *)
BEGIN (* Main *)
    Get_Data_From_CAMAC( Data ):
    (* Find number of data points *)
    FP := 1;
    WHILE Data[FP] < > 0 DO FP := FP + 1;
    IF (FP < 2 ) THEN Error (* Bad data ... exit *)
    (* Calculate scan width in GHz *)
    Scan_Width := (FP - 1) / (Data[FP] - Data[1] ) * FP_Size *
        Max_Clocks;
    (* Determine peak nonlinearity error *)
    Scan_Linearity( Data, FP, Peak_Error );
    (* Display the results. It may be desireable to do some averaging
before displaying, say 4 or 5 samples. A warning could be displayed if the
peak_error exceeds some limit. *)
    Display( Scan_Width, Peak_Error );
END.
```

What is claimed is:

1. Apparatus for scanning the frequency of a laser to provide a scanning laser beam having a scan width defined by a lower frequency and an upper frequency comprising:

a Brewster plate disposed in the path of a laser beam, the frequency of said laser beam being varied at the output of said Brewster plate by changing the instantaneous path length of said laser beam through the Brewster plate to provide said scanning laser beam, the Brewster plate being rotatable to vary the instantaneous path length of said laser beam through the Brewster plate;

means for rotating the Brewster plate to vary the instantaneous path length of said laser beam, thereby scanning the frequency of the laser beam between said lower frequency and said upper frequency to provide said scanning laser beam;

a interferometer disposed to receive at least a portion of said scanning laser beam and produce an output signal each time a frequency of said scanning laser beam crosses a free-spectral resonant mode of a resonant cavity of said interferometer, the number of output signals per unit time indicating the instantaneous frequency of said scanning laser beam;

a controller coupled to receive said output signals from said interferometer, said controller continually calculating the instantaeous frequency from said output signals per unit time received from the interferometer and thereafter continually determining the scan width from the instantaneous frequency, said controller further controlling said means for rotating the Brewster plate to vary the frequency of the scanning laser beam to provide the scanning laser beam wherein said controller further calculates a laser scan linearity of said scanned laser beam by comparing time differences between adjacent pairs of output signals and calculating the variation in those time difference for a selected number of contiguous output signals.

2. Apparatus as recited in claim 1 wherein said interferometer is a Fabry-Perot interferometer.

3. Apparatus as recited in claim 1 wherein said controller further includes means for controlling said means for rotating to provide a selectable scan width and a selectable scan frequency of said scanned beam.

* * * * *